(12) United States Patent
Morley (10) Patent No.: US 12,070,419 B2
(45) Date of Patent: Aug. 27, 2024

(54) IRIS REGISTRATION METHOD AND SYSTEM

(71) Applicant: Lensar, Inc., Orlando, FL (US)

(72) Inventor: Dustin Morley, Rocklege, FL (US)

(73) Assignee: Lensar, Inc., Orlando, FL (US)

( * ) Notice: Subject to any disclaimer, the term of this patent is extended or adjusted under 35 U.S.C. 154(b) by 71 days.

(21) Appl. No.: 17/373,375

(22) Filed: Jul. 12, 2021

(65) Prior Publication Data

US 2022/0142816 A1    May 12, 2022

Related U.S. Application Data (63) Continuation of application No. 14/444,366, filed on Jul. 28, 2014, now Pat. No. 11,090,190.

(60) Provisional application No. 61/891,149, filed on Oct. 15, 2013.

(51) Int. Cl.
*A61F 9/008*    (2006.01)

(52) U.S. Cl.
CPC .... *A61F 9/008* (2013.01); *A61F 2009/00846* (2013.01); *A61F 2009/00855* (2013.01)

(58) Field of Classification Search
CPC . A61F 2009/00846; A61F 2009/00855; G06T 7/003
See application file for complete search history.

(56) References Cited

U.S. PATENT DOCUMENTS

| | | | |
|---|---|---|---|
| 4,538,608 A | 9/1985 | L'Esperance | |
| 4,764,930 A | 8/1988 | Bille | |
| 4,901,718 A | 2/1990 | Bille | |
| 4,907,586 A | 3/1990 | Bille | |
| 5,098,426 A | 3/1992 | Sklar | |
| 5,246,435 A | 9/1993 | Bille | |
| 5,355,181 A | 10/1994 | Ashizaki | |
| 5,439,462 A | 8/1995 | Bille | |
| 5,480,396 A | 1/1996 | Simon | |
| 6,004,314 A | 12/1999 | Wei | |
| 6,099,522 A | 8/2000 | Knopp | |

(Continued)

FOREIGN PATENT DOCUMENTS

WO    WO 03/102498    12/2003

OTHER PUBLICATIONS

Oct. 30, 2015, WIPO, PCT Opinion PCT/US2015/042381.

(Continued)

*Primary Examiner* — Scott Luan
(74) *Attorney, Agent, or Firm* — Belvis Law, LLC.; Glen P. Belvis (57) ABSTRACT

A method that includes illuminating an eye with light at a first time and a second time and generating a first image of the eye based on the light that illuminates the eye at the first time. The method includes generating a second image of the eye based on the light that illuminates the eye at the second time. The method further includes positioning a laser source relative to the eye, wherein the laser source generates a therapeutic laser beam to be directed to the eye, wherein the first time is just prior to the therapeutic laser beam being directed to the eye and the second time is prior to the first time. The method further includes correcting orientation of the laser source relative to the eye based on a correlation function that is defined for the first and second images of the eye.

49 Claims, 6 Drawing Sheets

Iris boundary and eyelid interference detection for a CA-200F image

(56) References Cited

U.S. PATENT DOCUMENTS

| | | |
|---|---|---|
| 6,197,018 B1 | 3/2001 | O'Donnell |
| 6,312,422 B1 | 6/2001 | Dubnack |
| 6,322,556 B1 | 11/2001 | Gwon |
| 6,325,792 B1 | 12/2001 | Swinger |
| 7,655,002 B2 | 2/2010 | Myers |
| 8,262,646 B2 | 9/2012 | Frey |
| 8,382,745 B2 | 2/2013 | Naranjo-Tackman |
| 8,394,084 B2 | 3/2013 | Optimedica |
| 8,403,921 B2 | 3/2013 | Optimedica |
| 8,425,497 B2 | 4/2013 | Optimedica |
| 8,465,478 B2 | 6/2013 | Frey |
| 8,480,659 B2 | 7/2013 | Frey |
| 8,500,723 B2 | 8/2013 | Frey |
| 8,617,146 B2 | 12/2013 | Frey |
| 8,758,332 B2 | 6/2014 | Frey |
| 8,801,186 B2 | 8/2014 | Frey |
| 9,180,051 B2 | 11/2015 | Frey |
| 9,375,349 B2 | 6/2016 | Frey |
| 9,545,338 B2 | 1/2017 | Frey |
| 9,968,485 B2 | 5/2018 | Potter |
| 10,213,340 B2 | 2/2019 | Gray |
| 10,709,610 B2 | 7/2020 | Morley |
| 11,090,190 B2 | 8/2021 | Morley |
| 2002/0103478 A1 | 8/2002 | Gwon |
| 2003/0223037 A1* | 12/2003 | Chernyak ............. G06F 3/013 |
| | | 351/209 |
| 2005/0137586 A1 | 6/2005 | Grray |
| 2007/0173794 A1 | 7/2007 | Frey |
| 2007/0185475 A1 | 8/2007 | Frey |
| 2008/0287928 A1 | 11/2008 | Arnoldussen |
| 2010/0004641 A1 | 1/2010 | Frey |
| 2011/0190739 A1 | 8/2011 | Frey |
| 2012/0016350 A1 | 1/2012 | Myers |
| 2016/0095752 A1 | 4/2016 | Srinivasan |
| 2016/0302971 A1 | 10/2016 | Frey |
| 2017/0290703 A1 | 10/2017 | Teuma |
| 2018/0085256 A1 | 3/2018 | Gray |

OTHER PUBLICATIONS

Sep. 25, 2005, Chernyak, Method For Wavefront Registration, IE Transactions On Biomedical Engineering, vol. 52, No. 12, Dec. 2005.

* cited by examiner

Iris boundary and eyelid interference detection for a CA-200F image

FIG. 3

Approximating a circular arc using 3 line segments

FIG. 5

Example results of eyelid/eyelash interference detection

FIG. 7A          FIG. 7B

Iris boundary detection for treatment image

Image filtering procedure for eyelid interference detection

FIG. 8A

FIG. 8B
Unwrapped, DOG filtered iris (treatment top, topographer bottom)

FIG. 9  Correlation measures as a function of proposed cyclotorsion angle

FIG. 10A

FIG. 10B    Registration result

IRIS REGISTRATION METHOD AND SYSTEM

This application is a continuation of U.S. patent application Ser. No. 14/444,366 filed Jul. 28, 2014, which application claims pursuant to 35 U.S.C. § 119(e) the benefit of U.S. provisional application Ser. No. 61/891,149, filed Oct. 15, 2013, the entire disclosure of each of which are incorporated herein by reference.

BACKGROUND OF THE INVENTION

Field of the Invention

The present invention relates to method and system for registering an object, such as an iris of an eye, so that the object has a known orientation during a medical procedure.

Discussion of Related Art

The industry of ophthalmic surgical devices has seen rapid growth over the past couple decades. The use of Excimer lasers in procedures such as LASIK and PRK has become standard practice, and currently cataract surgery is undergoing a similar revolution with femtosecond lasers. In any ophthalmic surgery involving astigmatism correction, it is necessary to account for cyclotorsion, which is a significant rotation of the eye within the socket when a person transitions from standing or sitting up to lying down, as well as any small variations in head tilt or other patient-system alignment parameters. Generally speaking, diagnostic imaging for treatment planning is performed with the patient in an upright position while surgery is performed with the patient lying down, which opens the door for cyclotorsion to cause significant alignment error if not properly accounted for. Thus, in order to reliably use any information from a diagnostic imaging device (such as astigmatism axis) for incision planning, the ocular rotation difference between the diagnostic device and the surgical device must be determined so that the coordinate systems of the devices can be properly aligned.

Historically, cyclotorsion is accounted for by making ink marks along either the "vertical" or "horizontal" axis of the eye when the patient is standing up and using those ink marks as the reference axis when performing the surgical procedure. However, in the context of LASIK procedures, the VISX (Abbott Medical Optics) was the first to switch over to an automatic registration method using the iris patterns of the patient, which requires no ink marks and no manual intervention by the surgeon whatsoever. Automatic iris registration involves a surgical laser system receiving a picture of the patient's eye as seen by the diagnostic device when the treatment was planned, taking its own picture of the patient's eye, and registering the alignment between these two pictures using the iris patterns. To date, these algorithms have only been used in situations where the patient's eye has not undergone drug induced pupil dilation. Existing algorithms are all landmark based, meaning that specific points of interest in the iris are identified in both pre-treatment and treatment images and the registration is performed by matching these points between the two images.

However, in order to be usable in cataract surgery applications, it is necessary to have the patient's eye to undergo drug induced pupil dilation. Astigmatism correcting procedures as a part of cataract surgery typically involve partial thickness arcuate incisions, full thickness clear corneal incisions, tonic intra-ocular lenses, or a combination of the three. There is the possibility for all of these methods to greatly benefit from accurately accounting for cyclotorsion using automatic iris registration.

SUMMARY

One aspect of the present invention regards a method that includes illuminating an eye with light at a first time and a second time and generating a first image of the eye based on the light that illuminates the eye at the first time. The method further includes generating a second image of the eye based on the light that illuminates the eye at the second time. The method further includes positioning a laser source relative to the eye, wherein the laser source generates a therapeutic laser beam to be directed to the eye, wherein the first time is just prior to the therapeutic laser beam being directed to the eye and the second time is prior to the first time. The method further includes correcting orientation of the laser source relative to the eye based on a correlation function that is defined for the first and second images of the eye.

A second aspect of the present invention regards a laser therapeutic system that include a laser source that emits a therapeutic laser beam toward an eye and a laser control system that is in communication with the laser source, wherein the laser control system controls one or more parameters of the therapeutic laser beam. The system includes an analyzer that has a light source that illuminates the eye and one or more detectors that receive reflected light off from the eye and generate images of the eye. The analyzer further includes a memory containing computer executable instructions and a processor in communication with the laser control system, the one or more detectors and the memory, wherein the processor receives the images of the eye and executes the computer executable instructions so as to generate a signal based on a correlation function that is defined for the images of the eye and the signal is able to correct orientation of the therapeutic laser beam relative to the eye. Furthermore, the signal is received by the laser control system, which uses the signal to change orientation of the therapeutic laser beam relative to the eye.

One or more of the above mentioned aspects of the present invention provide the advantage of allowing for registration of an iris when drug induced pupil dilation is used for medical procedures, such as cataract surgery applications and astigmatism correcting procedures as a part of cataract surgery typically involve partial thickness arcuate incisions, full thickness clear corneal incisions, toric intra-ocular lenses, or a combination of the three.

One or more of the above mentioned aspects of the invention provide the advantage of accurately accounting for cyclotorsion.

BRIEF DESCRIPTION OF THE DRAWINGS

FIGS. 6 (a)-(f) show an embodiment of a process for reducing eyelid interference per the process shown in FIG. 2;

FIGS. 7 (a)-(b) show possible images showing the results of reducing eyelid and eyelash interference per the process shown in FIG. 2;

FIGS. 8 (a)-(b) show possible images showing the results of unwrapping an image of an iris and performing DOG filtering per the process shown in FIG. 2;

FIGS. 10 (a)-(b) show possible images showing the results of registration per the process shown in FIG. 2; and FIGS. 11 (a)-(b) show graphs of possible correlation measures vs. cyclotorsion angle relationships per the process shown in FIG. 2.

DESCRIPTION OF THE EMBODIMENTS

Figure 1:
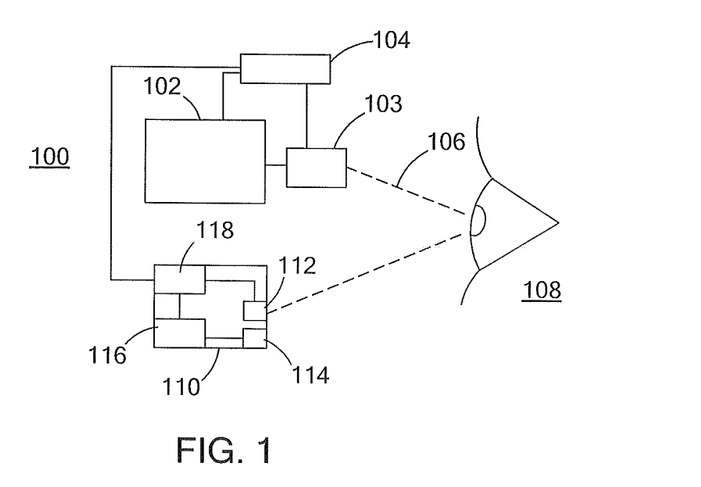
FIG. 1 schematically shows an embodiment of a laser therapeutic system in accordance with the present invention.

As schematically shown in FIG. 1, a laser therapeutic system 100 includes a laser source 102, laser optics 103, and a laser control system 104 in communication thereto. The laser source 102 generates a therapeutic laser beam 106 that is directed to an eye 108 of a patient via optics 103. The laser beam 106 is used to perform a variety of medical procedures on the eye 108, such as capsulotomies, lens fragmentation, and corneal incisions. The control system 104 via its communication with the optics 103 and the laser source 102 controls a number of parameters of the laser beam, such as direction, pulse width, and pulse rate. Examples of a possible laser source 102, optics 103, and laser control system 104 are disclosed in U.S. Pat. Nos. 8,262,646 and 8,465,478, the entire contents of each of which are incorporated herein by reference.

In communication with the laser source 102 and laser control system 104 is an analyzer 110. The analyzer 110 includes a light source 112 that illuminates the eye 108. One or more detectors or cameras 114 receive light reflected off the eye 108 and generate images of the eye 108. One image of the eye 108 is a pre-treatment image in that it is taken prior to the patient's eye 108 being subjected to the therapeutic laser beam 106. A second image of the eye 108 is a treatment image and is taken substantially at the time the eye 108 is treated by the therapeutic laser beam 106. The pretreatment and treatment images are stored in a recording medium, such as a memory 116, and are processed in a processor 118, which is in communication with the controller 104, memory 116 and light source 112. An example of an analyzer 110 that can be used is the Topcon CA-200F Corneal Analyzer manufactured by Topcon based in Japan.

Figure 2:
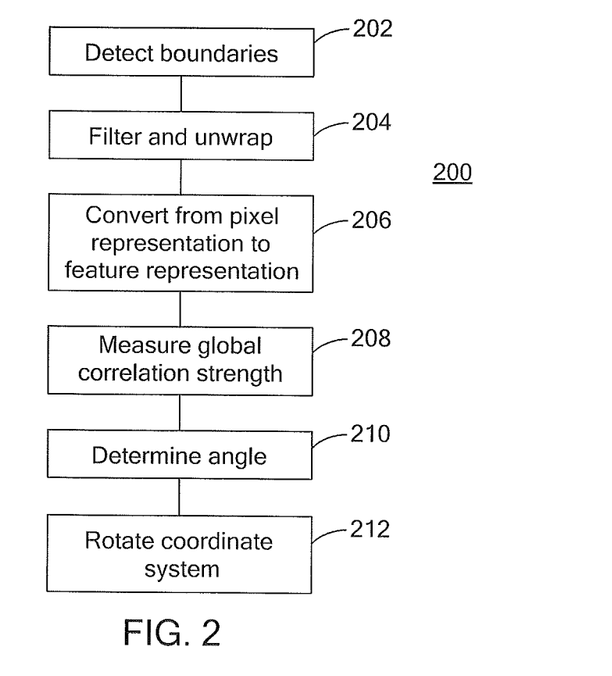
FIG. 2 shows a flow chart of an embodiment of method of registration of an object using the laser therapeutic system of FIG. 1 in accordance with the present invention.

The processor 118 executes instructions stored in the memory 116 so that an algorithm is performed in a very different approach from that used by existing algorithms. The algorithm proposed here is a global correlation algorithm, in which the registration is based on a correlation function that is defined for the pre-treatment and treatment images without singling out particular points in the iris. In operation, the eye 108 is imaged by the analyzer 110 prior to drug-induced dilation. Next, the eye 108 undergoes a laser procedure, such as cataract surgery, using the laser source 102 and laser control system 104. The basic steps/processes for the process or algorithm 200 are schematically shown in FIG. 2 and are as follows:

202—Detect Pupil-Iris and Iris-Sclera boundaries in both images, as well as any eyelid interference;
204—Filter and unwrap the iris in both images;
206—Convert the unwrapped images from pixel representation to feature representation, where each pixel gives rise to one feature vector;
208—Measure global correlation strength between feature maps for each possible angle of cyclotorsion;
210—Take the angle that gives the strongest correlation; and
212—Rotate the coordinate system accordingly.

In operation, the algorithm(s) related to processes 202-212 listed above are stored in the memory 116 as computer executable instructions, wherein the processor 118 executes the instructions so as to process the pre-treatment and treatment images so as to generate a signal that is able to correct the orientation of the therapeutic laser beam. Such signal is sent to the controller 104 which controls the optics 102 and laser source 103 so as to generate a correctly oriented laser beam 106.

Boundary Detection—Process 202

The easiest boundary to find is the pupil-iris boundary, as this boundary is extremely strong and the pupil itself is uniformly dark. An elliptical fit to the boundary is first found by approximating the center with a histogram method, performing a radial edge filter from this center on edges extracted with the standard canny algorithm, extracting up to 4 circles with a RANSAC algorithm, and combining matching circles together into an elliptical fit. An additional algorithm is used to fine-tune the result even further, which is basically a simplified implementation of Active Contours or Snakes. This algorithm takes as input the image and a previously found elliptical fit to the pupil boundary, and "explores" the image in the neighborhood of the boundary at several values of theta, finding the location that maximizes the radial component of the gradient of intensity values in the image for each theta. This builds a list of points that describe the boundary point by point in polar coordinates (with the origin remaining the center of the previously found ellipse). A simple Gaussian smoothing is then performed on this list of points to enforce continuity. The smoothed list of points is then taken to be pupil boundary.

Figure 3:
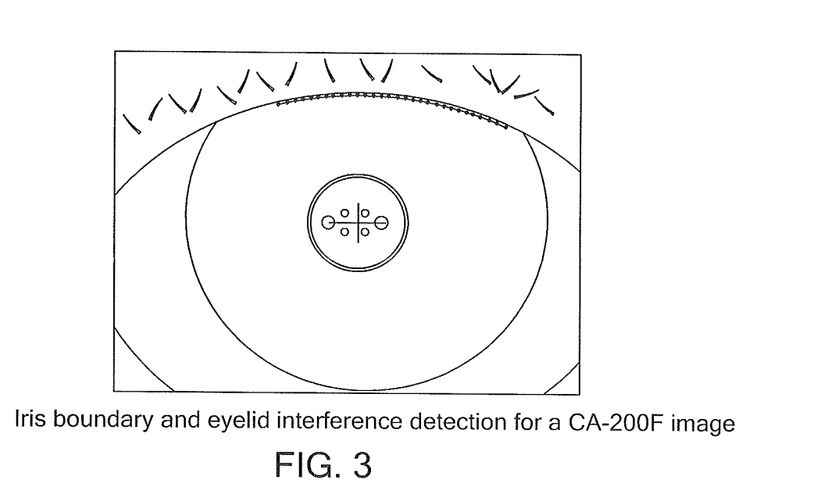
FIG. 3 shows a possible image used for performing an embodiment of a process for detecting a boundary of an iris and eyelid interference per the process shown in FIG. 2.

To find the iris-sclera boundary in the diagnostic image of FIG. 3, for example, a circular splines algorithm is used, which traverses through an appropriately restricted three dimensional parameter space (center and radius of a circle) treating distinct angular regions separately, seeking to maximize the dot product between the gradient and the outward normal of the circle splines. The basic algorithm structure can be formulated as the following: for each choice of center and radius, form a circle and assign a score for this circle to each angular region from the radial component of the gradient; for each angular region for which the score obtained with this circle is higher than the previous high score for that angular region, store the new high score and the circle that achieved it. This results in a set of circular splines which are then filtered, removing splines that don't fit very well with the others. Eight splines are used for the image in FIG. 3, thus rendering eight separate angular regions of 45 degrees each.

Figure 4:
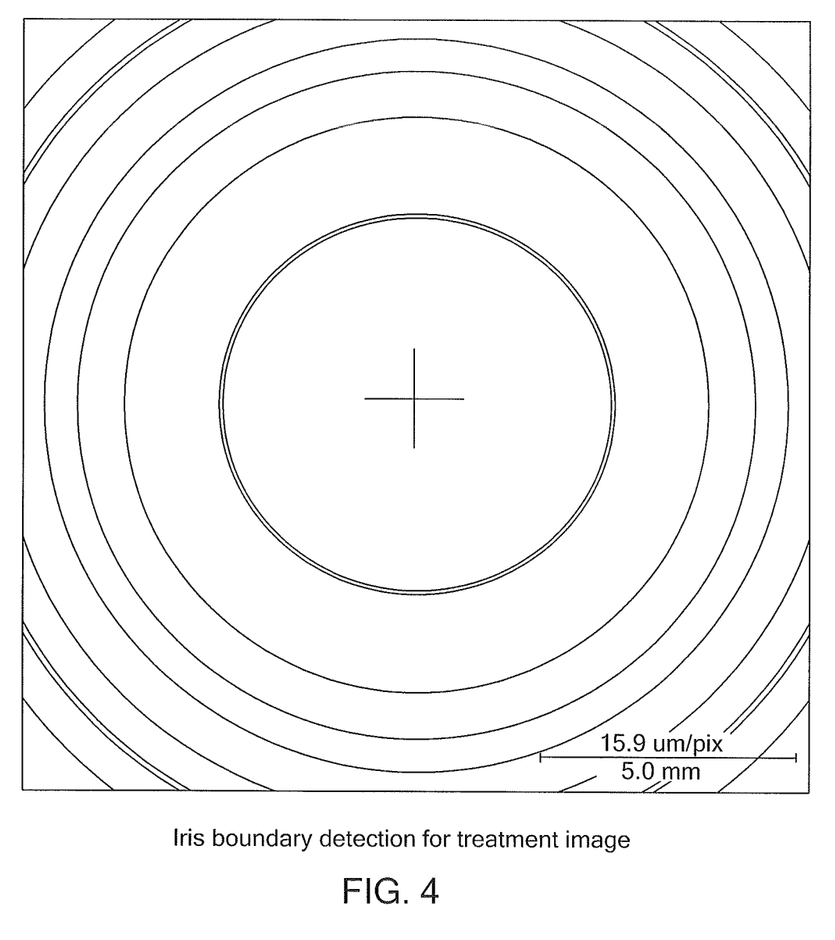
FIG. 4 shows a possible treatment image used for performing an embodiment of a process for detecting a boundary of an iris per the process shown in FIG. 2.

To find the iris-sclera boundary in the treatment image, the ellipse describing the limbus in the diagnostic image is transferred to the treatment image by scaling the two radii of the ellipse according to the differing resolutions of the two cameras, assuming no cyclotorsion in placing the axis of the ellipse, and assuming that in the treatment image the limbus will be approximately concentric with the dilated pupil. This constitutes a good initial approximation, which is then improved upon by first using the same snakes algorithm that is used for the pupil boundary and then fitting an ellipse to the resulting set of points.

Figure 5:
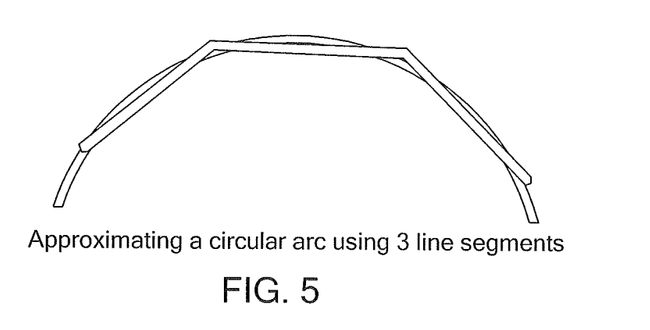
FIG. 5 schematically shows a possible way of approximating a circular arc during performance of an embodiment of a process for detecting a boundary of an iris and eyelid interference per the process shown in FIG. 2.

Often, images taken at a diagnostic device, such as analyzer 110, have some degree of eyelid or eyelash interference concealing a portion of the iris. To mask out these regions from consideration in the registration algorithm, eyelid/iris boundaries must be segmented in an image obtained from analyzer 110, such as shown in FIG. 6 (a). The first step in the segmentation is to detect all small glints in the image, as there tends to be several of these small glints in the neighborhood of eyelid/iris boundaries. Next, a Difference-Of-Gaussians (DOG) filter is applied, which has been empirically parameterized to remove eyelid/iris boundaries from the image (i.e. the area containing the boundary becomes dark) and converts image (a) from FIG. 6 to the image of FIG. 6(b). The image is then converted to an inverted binary image—all pixels below a certain threshold are made white, and all other pixels are made black, resulting in image FIG. 6(c). Pixels belonging to small glints are then "filled in" (i.e., made white). The resulting image has a very thick white edge representing the eyelid or eyelash interference with the iris, as well as some extraneous smaller white edges. These extraneous edges are then filtered out by a novel algorithm utilizing the integral image concept, which produces the image of FIG. 6(d). The underlying concept is similar to the classical "erode" algorithm that is often used for getting rid of small extraneous clusters of edges, with the difference being that the average intensity in the "neighborhood" of a white pixel determines whether it is kept or removed, as opposed to the amount of its neighbors that are white making the determination. The "neighborhood" is shaped according to what is expected for the eyelid. The eyelid can be represented quite well by a low-curvature circle, which can be crudely approximated by a "trapezoid top" shape. Thus, each pixel is given three chances to pass an integral image test: one with a horizontal rectangle, one for each of two parallelograms tilted 45° as shown in FIG. 5.

Figure 6A:
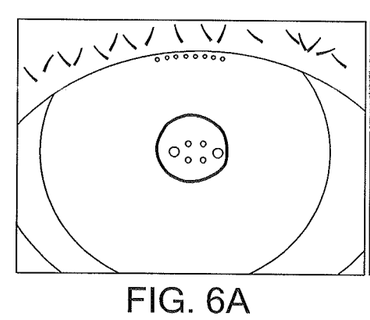
Figure 6B:
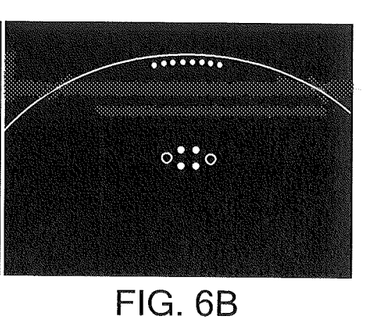
Figure 6C:
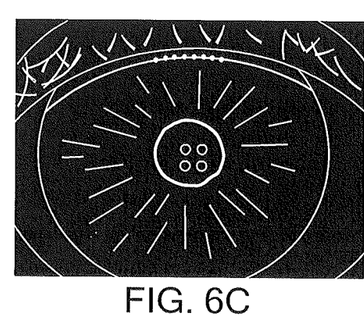
Figure 6D:
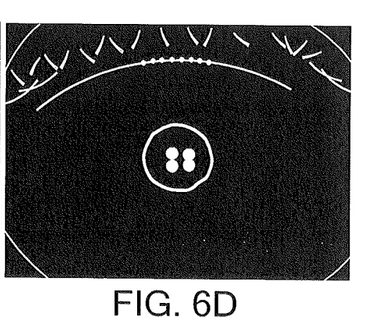
Figure 6E:
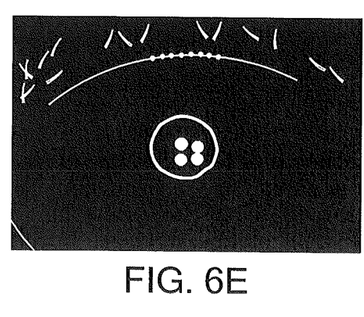

If the threshold for minimum average intensity is met in either one of these three tests, the pixel remains white; otherwise the pixel is made black. Then, a circular mask is applied to mask out areas that are too close to the top and bottom borders of the image to be considered, and the classical erode algorithm is applied to thin out the eyelid/eyelash interference region as well as get rid of any lingering undesired edges, resulting in the image of FIG. 6(e). The reason why the novel "erode-like" algorithm is used in the first place is because the "erode-like" algorithm described here gets rid of the vast majority of the undesired edges while essentially leaving the edges of interest completely intact, allowing for the classical erode algorithm to simply finish the job. If this algorithm is skipped in favor of using only the classical erode algorithm, it becomes impossible to have a threshold that gets rid of all extraneous edges without also getting rid of large chunks of the eyelid/eyelash interference region. Basically, this algorithm allows for a decoupling of filtering out tiny extraneous edges and thinning out thick boundaries.

Figure 6F:
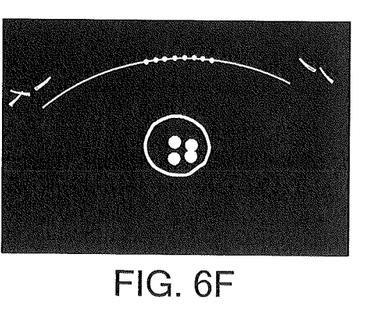
Figure 7A:
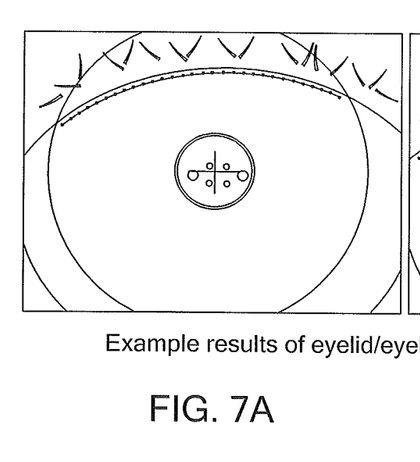
Figure 7B:
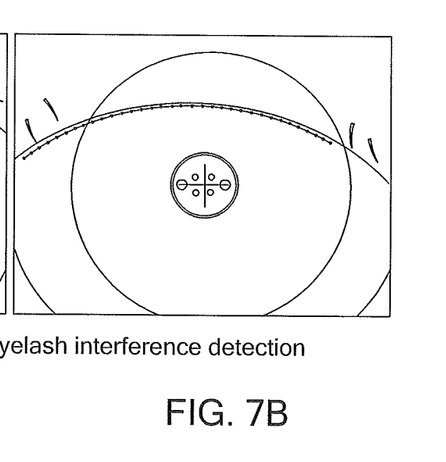

Finally, a bottom-up filter is applied to the upper eyelid region resulting in the image of FIG. 6(f) and a top-down filter to the lower eyelid region, and a RANSAC circle finding algorithm is used on the resulting image to extract the best circle for each eyelid. The RANSAC algorithm is restricted to the area above the pupil for the upper eyelid and the area below the pupil for the lower eyelid (in other words, the pupil is masked out). If RANSAC is unable to find a curve containing at least an empirically determined number of pixels, it is assumed that there is no (or negligible) eyelid interference. If eyelid interference is found, then the region of interference is masked out of both the iris-sclera boundary detection algorithm and the registration algorithm. Example results for eyelid/eyelash interference detection are shown in FIGS. 7A-B.

Filtering and Unwrapping the Iris—Process 204

The iris during dilation is approximated by a rubber sheet model, such that the iris in the non-dilated eye is assumed to basically be a stretched out version of the iris in the dilated eye. In this approximation, a pseudopolar mapping is carried out to unwrap the iris into a rectangular image in which the dimensions represent angle and distance from the inner (pupil) boundary. If the boundary detection is perfect, then the top row of this image will perfectly represent the pupil boundary and the bottom row will perfectly represent the sclera boundary. The size of the averaging area used to fill each pixel in the unwrapped image increases linearly as a function of distance from the pupil center. Obviously, there is technically information loss associated with this approach, with the amount of information loss increasing with distance from the pupil center. However, this loss does not have any noticeable impact, and in fact running registration algorithms on these images rather than the original images results in both a cleaner implementation and faster run time.

Figure 8A:
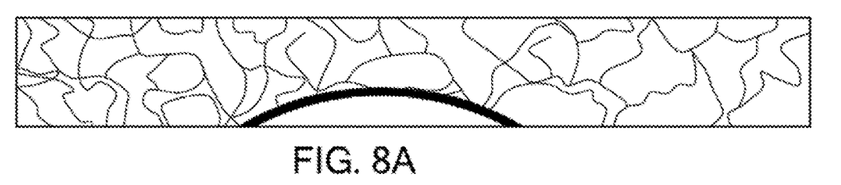
Figure 8B:
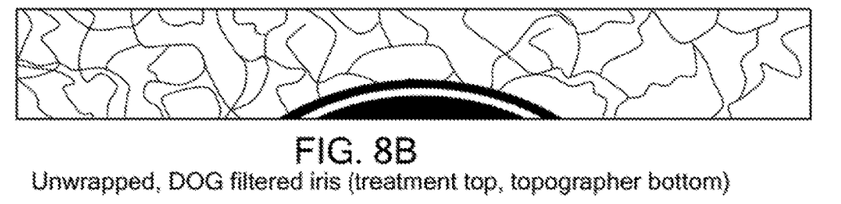

After unwrapping, the images are filtered with a Difference-Of-Gaussians (DOG) technique. This technique simply involves subtracting a severely blurred version of the image from a slightly blurred version of the image, which is in effect a band pass filter in the frequency domain. The result is increased signal strength of the iris fibers. An example of an unwrapped, DOG filtered iris is shown in FIGS. 8A-B.

Feature Extraction—Process 206

A feature vector is built for each unwrapped iris image, with the content of the feature vector being derived from gradient information from the structure tensor and Gabor filters. Thus, the components of the image feature vector are themselves "local" feature vectors with one Gabor filter component and one structure tensor component, and each of these two components are vectors themselves. Gabor filters are used by J. Daugman in his iris recognition algorithms (see http://www.cl.cam.ac.uk/~jgd1000/csvt.pdf and U.S. and U.S. Pat. No. 5,291,560, the entire contents of which are incorporated herein by reference). The information extracted from the Gabor filter is a point in the complex plane which is computed by convolving a 2D Gabor wavelet with an area of the iris, according to the formula below:

$$\int_\rho \int_\varphi I(\rho, \varphi) e^{-i\omega(\theta_0 - \varphi)} e^{\frac{-(r_0-\rho)^2}{\alpha^2}} e^{\frac{-(\theta_0-\varphi)^2}{\beta^2}} \rho \, d\rho \, d\theta$$

Where $\alpha$, $\beta$, and $\omega$ are wavelet size and frequency parameters, $(r_0, \theta_0)$ is the point about which the area of the iris being considered is centered, and I is the intensity value of the unwrapped iris image at a given point. In discrete form, this equation is applied as follows:

$$\text{Real Part} = \sum_{\varphi=\theta_-}^{\theta_+} \sum_{\rho=r_-}^{r_+} I(\rho, \varphi) \cos(\omega(\varphi - \theta_0)) e^{\frac{-(r_0-\rho)^2}{\alpha^2}} e^{\frac{-(\theta_0-\varphi)^2}{\beta^2}}$$

-continued $$\text{Imaginary Part} = \sum_{\varphi=\theta_-}^{\theta_+} \sum_{\rho=r_-}^{r_+} I(\rho, \varphi)\sin(\omega(\varphi-\theta_0))e^{\frac{-(r_0-\rho)^2}{\alpha^2}}e^{\frac{-(\theta_0-\varphi)^2}{\beta^2}}$$

Where $\theta_-$, $\theta_+$, $r_-$, and $r_+$ denote the boundaries of the shell-like region over which the computation is done. For unwrapped images, $\varphi$ becomes x, $\rho$ becomes y, and the region is rectangular rather than shell-like. This allows for a simple and computationally fast implementation, which is to set $r_0$ and $\theta_0$ to zero and fill a 2D array with values according to the above equations with the image intensity values removed, for each the real part and imaginary part, and then convolve these 2D arrays with the images. This yields, at every pixel of each image, a 2D vector with components for the real and imaginary part of the result of centering a gabor filter on that pixel.

Similarly, the structure tensor is used to extract gradient information in the local neighborhood of each pixel. The entries in the 2×2 matrix representing the structure tensor are filled by averaging the derivative-based quantity over the entire neighborhood. Then, the eigenvalues and eigenvectors are extracted from the resulting matrix. The eigenvectors and eigenvalues give the dominant gradient direction and a measure of the strength of the gradient, respectively.

$$S(x, y) = \begin{pmatrix} f_x^2 & f_x f_y \\ f_y f_x & f_y^2 \end{pmatrix}$$

Measuring Correlation Strength—Process 208

Consider the filtered, unwrapped image taken at the time of surgery $I_1$ and the filtered, unwrapped image taken prior to surgery $I_2$. Define an inner product for the structure part of the feature vectors of the two images given a particular hypothesized angle of cyclotorsion $\delta$ and a radial shear function $\xi_\delta(x)$ (to allow room for errors in boundary detection and the rubber sheet model approximation) as follows:

$$P_S(I_1, I_2, \delta) = \left(\frac{1}{N_S}\right)\sum_{x,y} \frac{\overrightarrow{\nabla I_1}(x, y) \cdot \overrightarrow{\nabla I_2}(x+\delta, y+\xi_\delta(x))}{|\overrightarrow{\nabla I_1}(x, y)||\overrightarrow{\nabla I_2}(x+\delta, y+\xi_\delta(x))|}$$

Similarly, we define an inner product for the Gabor wavelet part of the feature vectors as follows:

$$P_G(I_1, I_2, \delta) = \left(\frac{1}{N_G}\right)\sum_{x,y} \frac{\overrightarrow{G_1}(x, y) \cdot \overrightarrow{G_2}(x+\delta, +\xi_\delta(x))}{|\overrightarrow{G_1}(x, y)||\overrightarrow{G_2}(x+\delta, +\xi_\delta(x))|}$$

With $\overrightarrow{G_m}(x, y)$ a 2D vector corresponding to the complex number that results from applying the Gabor filter to image m at the point (x,y). Some (x,y) points are ignored either due to local saturation or being too close to identified regions of eyelid interference or the image boundary. Additionally, thresholding is done for both the gradient features and the Gabor features, such that only the top 75% (according to magnitude of the complex plane vector) of the Gabor features are kept and only the top 75% (according to value of the smaller eigenvalue) of the gradient features are kept. Thus, for each metric, the summation is taken only over values that are kept for that metric and normalized to the number of such values. As was previously mentioned, to allow room for a little bit of errors in boundary detection and/or the rubber sheet model itself, a small radial shear is allowed, and computed as follows. At each angular location (x-coordinate) and cyclotorsion angle $\delta$, scores are computed for different values of a radial offset $\xi_\delta(x)$ (an offset applied to the y-coordinate) and note is taken of which value of $\xi_\delta(x)$ (denoted here as $\xi'_\delta(x)$) gives the strongest correlation for the radial registration line defined by x and $\delta$. To enforce continuity of the shear for each cyclotorsion angle $\delta$, $\xi_\delta(x)$ is chosen according to the following simple averaging function:

$$\xi_\delta(x) = \frac{1}{2w+1} \sum_{x'=x-w}^{x+w} \xi'_\delta(x')$$

When doing this computation, w needs to be large enough to prevent $\xi_\delta(x)$ from being completely chaotic but not so large as to ruin the whole point of allowing a varying radial offset. For example, 10° has been observed to work well. Once the function $\xi_\delta(x)$ is computed for each $\delta$, the inner products as defined in the equations at the beginning of this section can readily be computed.

A strong correlation corresponds to large values of both inner products. The domain of both inner products is [−1, +1]—thus, the net correlation is based on the average of the two inner products. Over a range of +−18°, a reasonable biological limit for cyclotorsion, the net correlation is computed from the average of the two inner products.

$$C(\delta) = \frac{P_S(\delta) + P_G(\delta)}{2}$$

Figure 9:
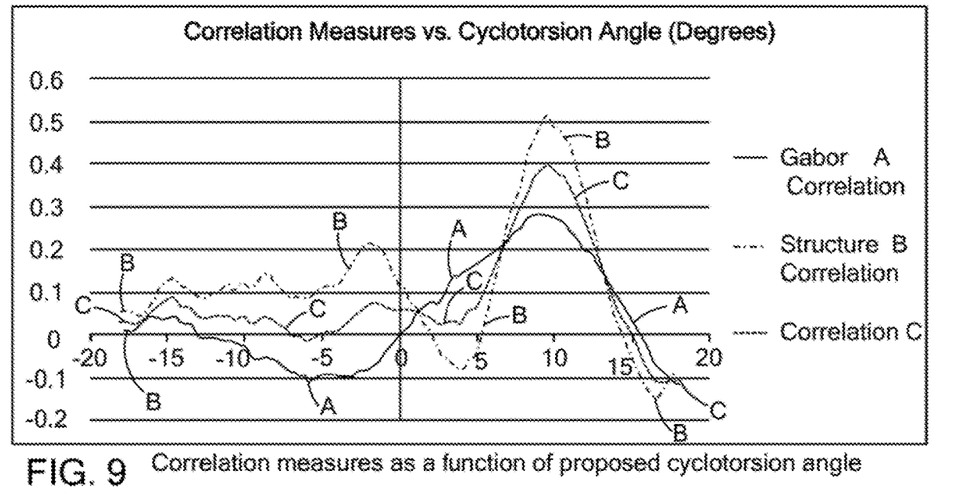
FIG. 9 shows a graph of a possible correlation measures vs. cyclotorsion angle relationship per the process shown in FIG. 2.

An example of correlation measurements as a function of proposed cyclotorsion angle is shown in FIG. 9.

Extracting and Applying the Angle of Cyclotorsion—Processes 210 and 212

The angle of cyclotorsion is the angle that produces the maximum correlation strength between the extracted features, which corresponds to the global maximum of the curve C in FIG. 9. A confidence score T is computed based on how strong the global maximum is relative to the next highest local maximum, according to the following formula:

$$\tau = 100*(1-10^{1-r})$$

Where r is the ratio between the global maximum and the next largest local maximum present in the correlation function after Gaussian smoothing. For example, in the smoothed correlation function for the plot in FIG. 9, the global maximum is at +9.5 degrees, and the next strongest local maximum occurs at −14.5 degrees. From the unsmoothed correlation function, the correlation strengths at these cyclotorsion angles are 0.39 and 0.08 respectively; hence r=4.88 and the resulting confidence score is practically 100. Note that r=1 produces a confidence score of 0, r=2 produces a confidence score of 90%, and it is impossible to obtain a score larger than 100 or less than zero (because r is guaranteed to be greater than or equal to 1). The confidence score is multiplied together with the correlation strength at the global maximum of the unsmoothed correlation function (exactly as seen in the plot above) to obtain a final score which can be used to decide whether the registration was successful or not based on an experimentally determined threshold (see the validation section). This constructs a confidence metric that is both dependent on the absolute value of the correlation strength and the value of the correlation strength relative to the next most convincing peak in the correlation function. It is important for the metric to depend on both of these—one can imagine that if the two highest peaks were of the exact same height it would certainly not be sensible to arbitrarily pick one. Similarly, regardless of the relative score, an absolute correlation strength significantly less than that of all image pairs verified to be correctly registered should not be trusted.

In the left-handed natural coordinate system of the images, the cyclotorsion angle computed tells what value of angle in the topographer image was lined up with the zero angle in the treatment image. In the right-handed coordinate system (where counter clockwise corresponds to positive values of theta), this is equivalent to how the topographer image would be rotated to line up with the treatment image. This is the number needed, because treatment was planned in the frame of reference of the topographer image. Thus, for a cyclotorsion angle of 9.5 degrees, the compass defining the angular coordinate system on the laser system should be rotated by +9.5 degrees. This angle of rotation is calculated by processor 118 and conveyed to the controller 104 which rotates the laser beam 106.

Figure 10A:
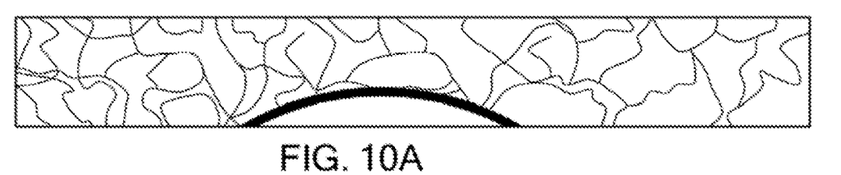
Figure 10B:
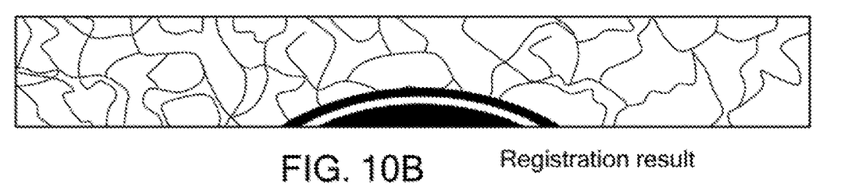

As shown in FIGS. 10A-B, there are four regions of particular high correlation at the proposed angle of cyclotorsion. In all four regions it is readily observed that these really do look like the same patches of the iris in both images. In several locations the behavior of the iris under dilation is somewhat nonlinear—see, for example, how the bright fiber just to the right of the leftmost region slightly changes shape between the two images. This illustrates the nature of the registration under deformation problem and sheds some light on why the algorithm used here is the right approach for this type of problem. Deformation in this problem essentially corresponds to iris fibers between the two unwrapped images changing slightly in length, shape, and/or orientation relative to the pupil boundary (hence here we are only discussing the part of the deformation that is not accounted for by the rubber sheet model). Small changes in length, shape, and orientation will in general cause small rotations of the eigenvectors of the structure tensor, which is by no means drastic to a correlation based on the inner product between these eigenvectors. These small deformations are also concentrated in the domain of higher frequencies rather than lower frequencies, and Gabor wavelets mainly extract information from lower frequencies. Thus, both correlation metrics used here are theoretically capable of handling small deformations in image registration.

Figure 11A:
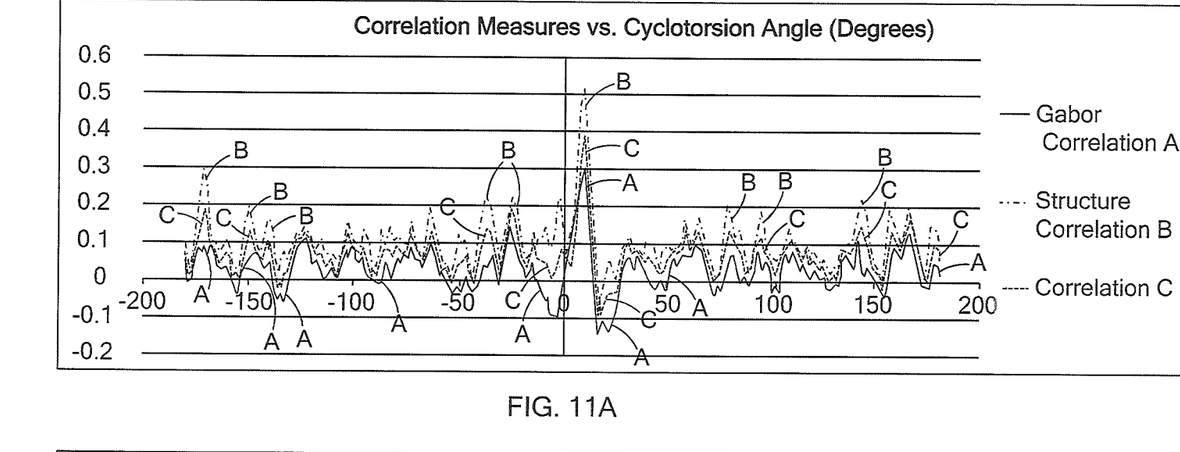
Figure 11B:
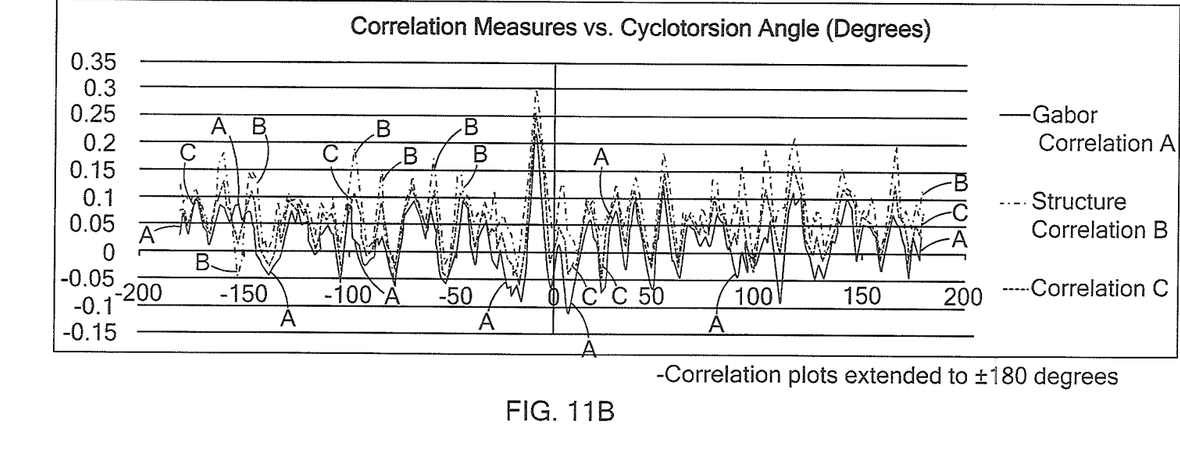

Some significant statistical validation is possible as well. One example method for doing this is to extend the allowable range of cyclotorsion angles all the way out to +180° to verify that the global maxima remains at the same location and examine how strong of a maxima it is relative to the correlation strengths of all other cyclotorsion angles. A couple of examples are shown in FIGS. 11(*a*)-(*b*). In these plots, it is observed that there seems to be a fundamental limit on how strong of a correlation can be obtained from an incorrect cyclotorsion angle.

Accounting for cyclotorsion is of paramount importance in any refractive surgery focused on correcting and/or compensating for astigmatism. An algorithm is proposed that should be able to solve this problem in cataract surgery either in the context of astigmatism-correcting incisions or assistance in tonic IOL positioning. One exciting aspect of applying iris registration to cataract surgery is the prospect of releasing the first iris registration algorithm that can accommodate drug induced pupil dilation.

From the foregoing description, one skilled in the art can readily ascertain the essential characteristics of this invention, and without departing from the spirit and scope thereof, can make various changes and/or modifications of the invention to adapt it to various usages and conditions.

What is claimed:

1. A therapeutic system, comprising:
 a) a laser source; comprising a laser, laser optics and a coordinate system for directing the delivery of a therapeutic laser beam from the laser source to an eye of a patient;
 b) a processor; the processor configured to execute instructions stored in a memory; and,
 c) a control system; wherein the control system is in communication with the processor and the laser source;
 d) wherein the memory is configured to have a pre-treatment image of an iris of the eye of the patient and a treatment image of the iris of the eye of the patient;
 e) wherein the instructions comprise:
  i) a global correlation algorithm configured to determine a correlation function for registration of the eye based upon the pre-treatment and treatment images; and,
  ii) wherein the algorithm is configured to determine the correlation function, without singling out particular points in the pre-treatment and treatment images;
 f) whereby the laser system is configured to align the coordinate system based at least in part upon the correlation function.

2. The system of claim 1, wherein the global correlation algorithm is configured to perform the processes comprising:
 a) detect a pupil-Iris boundary in both the pre-treatment and treatment images;
 b) filter and unwrap the iris in both the pre-treatment and treatment images;
 c) convert the both the pre-treatment and treatment unwrapped images from pixel representations to feature representations;
 d) measure a global correlation strength between the feature representations for a plurality of possible angles of cyclotorsion; and,
 e) identify the angle of cyclotorsion that gives a strongest correlation.

3. The system of claim 1, wherein the system comprises the pre-treatment image.

4. The system of claim 1, wherein the eye in the pre-treatment image is dilated.

5. The system of claim 1, comprising an analyzer.

6. The system of claim 5, wherein the processor is contained in the analyzer.

7. The system of claim 5 or 6, wherein the analyzer further comprises a light source, and a detector.

8. The system of claim 2, wherein the system comprises the pre-treatment image.

9. The system of claim 8, wherein the eye in the pre-treatment image is dilated.

10. The system of claim 2, comprising an analyzer.

11. The system of claim 10, wherein the processor is contained in the analyzer.

12. The system of claim 10 or 11, wherein the analyzer further comprises a light source, and a detector.

13. The system of claim 1, 2, 3, 8 or 9, wherein the system comprises the treatment image.

14. The system of claim 3, 4, 8, or 9, wherein the patient was in an upright position when the pre-treatment image was obtained.

15. The system of claim 1, 2, 3, 8 or 9, wherein the system comprises the treatment image; and, wherein the patient was in a lying down position when the treatment image was obtained.

16. The system of claim 1, 2, 3, 4, 8, or 9, wherein the laser is a femto second laser.

17. A therapeutic system, comprising:
   a) a laser source; comprising a laser, laser optics and a coordinate system for directing the delivery of a therapeutic laser beam from the laser source to an eye of a patient;
   b) an analyzer comprising a processor and a memory; and configured to execute instructions stored in the memory;
   c) wherein the memory is configured to receive a pre-treatment image of an iris of the eye of the patient and a treatment image of the iris of the eye;
   d) wherein the instructions comprise:
      i) an algorithm configured to determine a registration function for registration of the eye based upon the pre-treatment and treatment images; and,
      ii) wherein the algorithm is configured to determine the registration function, without singling out particular points on the iris in the pre-treatment and treatment images;
      iii) wherein the algorithm is configured to unwrap both the pre-treatment and treatment images into rectangular images having dimensions,
      iv) wherein a first row of the rectangular images represent a pupil boundary of the eye; and a second row of the rectangular images represent a sclera boundary of the eye;
      v) wherein the dimensions of the rectangular images represent an angle and a distance from the pupil boundary;
   e) wherein the laser system is configured to align the coordinate system based in part on the registration function.

18. A therapeutic system, comprising:
   a) a laser source; comprising a laser, laser optics and a coordinate system for directing the delivery of a therapeutic laser beam from the laser source to an eye of a patient;
   b) an analyzer comprising a processor and a memory; and configured to execute instructions stored in the memory;
   c) wherein the memory comprises a pre-treatment image of an iris of the eye of the patient in the upright position and a treatment image of the iris of the eye of the patient in a lying down position;
   d) wherein the instructions comprise:
      i) an algorithm configured to determine a registration function for registration of the eye based upon the pre-treatment and treatment images; and,
      ii) wherein the algorithm is configured to determine the registration function, without singling out particular points on the iris in the pre-treatment and treatment images;
      iii) wherein the algorithm is configured to unwrap both the pre-treatment and treatment images into rectangular images having dimensions,
      iv) wherein a first row of the rectangular images represents a pupil boundary of the eye; and a second row of the rectangular images represent a sclera boundary of the eye;
      v) wherein the dimensions of the rectangular images represent an angle and a distance from the pupal boundary;
   e) wherein the laser system is configured to align the coordinate system based in part on the registration function.

19. The system of claim 17 or 18, wherein the therapeutic laser beam is a femto second laser beam.

20. The system of claim 17 or 18, wherein the pre-treatment image of the eye is of a dilated pupil.

21. The system of claim 17 or 18, wherein the treatment image of the eye is of a dilated pupil.

22. The system of claim 17 or 18, wherein the analyzer further comprises a light source, and a detector.

23. The system of claim 17 or 18, wherein the pre-treatment image was taken on the patient in an upright position.

24. The system of claim 17 or 18, wherein the treatment image was taken on the patient in a lying down position.

25. A method of aligning a coordination system in a therapeutic system; wherein the therapeutic system comprises a laser source that emits a therapeutic laser beam toward an eye; a laser control system in communication with the laser source, wherein the laser control system controls a parameter of the therapeutic laser beam; and, an analyzer; wherein the analyzer comprises: a memory; executable instructions; and a processor; the method of aligning the coordination system comprising:
   a) receiving a pre-treatment image of eye;
   b) receiving a treatment image of the eye;
   c) unwrapping each image to provide a pre-treatment feature representation of the eye and a treatment feature representation of the eye;
   d) the analyzer determining a change in an orientation of an iris of the eye between the pre-treatment image and the treatment image, based upon the pre-treatment feature representation and the treatment feature representation; without singling out particular points in the pre-treatment and treatment images; and,
   e) aligning the coordinate system based upon the change in the orientation of the iris of the eye.

26. The method of claim 25, wherein the therapeutic laser beam is a femto second laser beam.

27. The method of claim 25, wherein: a) the pre-treatment feature representation is rectangular having a top row representing a pupil boundary of the eye; and a bottom row representing a sclera boundary of the eye; b) wherein the treatment feature representation is rectangular having a top row representing the pupil boundary of the eye; and a bottom row representing the sclera boundary of the eye; and, c) wherein the dimensions of the rectangular images represent an angle and a distance from the pupal boundary.

28. The method of claim 25, 26 or 27, wherein aligning the coordinate system comprises rotating the coordinate system.

29. The method of claim 25, 26 or 27, wherein the aligning of coordinate system corrects for a cyclotorsion of the eye.

30. The method of claim 25, 26 or 27, wherein the pre-treatment image of the eye is of a dilated pupil.

31. The method of claim 25, 26 or 27, wherein the treatment image of the eye is of a dilated pupil.

32. The method of claim 25, 26 or 27, wherein the analyzer further comprises a light source, and a detector.

33. The method of claim 25, 26 or 27, wherein the pre-treatment image was taken on the patient in an upright position.

34. The method of claim 25, 26 or 27, wherein the treatment image was taken on the patient in a lying down position.

35. A method of aligning a coordination system in a therapeutic system; wherein the therapeutic system comprises a laser source that emits a therapeutic laser beam toward an eye; a laser control system in communication with the laser source, wherein the laser control system controls a parameter of the therapeutic laser beam; and, an analyzer; wherein the analyzer comprises: a memory; executable instructions; and a processor; the method of aligning the coordination system comprising:
- a) receiving a treatment image of the eye;
- b) unwrapping a pre-treatment image of eye to provide a pre-treatment feature representation;
- c) unwrapping a treatment image of the eye to provide a treatment feature representation of the eye;
- d) the analyzer determining a change in an orientation of an iris of the eye between the pre-treatment image and the treatment image, based upon the pre-treatment feature representation and the treatment feature representation; without singling out particular points in the pre-treatment and treatment images; and,
- e) aligning the coordinate system based upon the change in the orientation of the iris of the eye.

36. The method of claim 35, wherein the therapeutic laser beam is a femto second laser beam.

37. The method of claim 35, wherein: a) the pre-treatment feature representation is rectangular having a row representing a pupil boundary of the eye; and an opposite row representing a sclera boundary of the eye; b) wherein the treatment feature representation is rectangular having a row representing the pupil boundary of the eye; and an opposite row representing the sclera boundary of the eye; and, c) wherein the dimensions of the rectangular images represent an angle and a distance from the pupil boundary.

38. The method of claim 35, 36 or 37, wherein aligning the coordinate system comprises rotating the coordinate system.

39. The method of claim 35, 36 or 37, wherein the aligning of coordinate system corrects for a cyclotorsion of the eye.

40. The method of claim 35, 36 or 37, wherein the pre-treatment image of the eye is of a dilated pupil.

41. The method of claim 35, 36 or 37, wherein the treatment image of the eye is of a dilated pupil.

42. The method of claim 35, 36 or 37, wherein the analyzer further comprises a light source, and a detector.

43. The method of claim 35, 36 or 37, wherein the pre-treatment image was taken on the patient in an upright position.

44. The method of claim 35, 36 or 37, wherein the treatment image was taken on the patient in a lying down position.

45. A method of compensating for a cyclotorsion of an eye; the method comprising:
- a) detecting a pupil-iris and an iris-sclera boundary in both a pre-treatment image of an eye, and a treatment image of the eye;
- b) filtering and unwrapping both images of the eye;
- c) converting the unwrapped images from a pixel representation to a feature representation, where each pixel gives rise to one feature vector;
- d) measuring a global correlation strength between a feature maps for each possible angle of cyclotorsion;
- e) deterring an angle that gives the strongest correlation; and
- f) aligning a coordinate system based upon the angle.

46. The system of claim 1, 17, or 18, wherein to align the coordinate system comprises to rotate the coordinate system.

47. The method of claim 1, 17 or 18, wherein the system corrects for a cyclotorsion of the eye.

48. The system of claim 17 or 18, wherein the first row is the top row of the rectangular images and the second row is the bottom row of the rectangular images.

49. The method of claim 45, wherein aligning a coordinate system comprises rotating the coordinate system.

* * * * *